United States Patent
Paul et al.

(10) Patent No.: US 10,980,429 B2
(45) Date of Patent: Apr. 20, 2021

(54) METHOD AND SYSTEM FOR CUFFLESS BLOOD PRESSURE ESTIMATION USING PHOTOPLETHYSMOGRAM FEATURES AND PULSE TRANSIT TIME

(71) Applicant: Tata Consultancy Services Limited, Mumbai (IN)

(72) Inventors: Sushmita Paul, Kolkata (IN); Anirban Dutta Choudhury, Kolkata (IN); Shreyasi Datta, Kolkata (IN); Arpan Pal, Kolkata (IN); Rohan Banerjee, Kolkata (IN); Kayapanda Mandana, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 544 days.

(21) Appl. No.: 15/901,866

(22) Filed: Feb. 21, 2018

(65) Prior Publication Data

US 2018/0235487 A1    Aug. 23, 2018

(30) Foreign Application Priority Data

Feb. 23, 2017   (IN) .............................. 201721006574

(51) Int. Cl.
*A61B 5/021*     (2006.01)
*A61B 5/024*     (2006.01)
(Continued)

(52) U.S. Cl.
CPC ........ *A61B 5/02125* (2013.01); *A61B 5/0245* (2013.01); *A61B 5/02416* (2013.01);
(Continued)

(58) Field of Classification Search
CPC ............ A61B 5/02125; A61B 5/02416; A61B 5/0245; A61B 5/0456; A61B 5/7264; A61B 5/7278; A61B 5/7282
(Continued)

(56) References Cited

U.S. PATENT DOCUMENTS 8,808,188 B2     8/2014  Banet et al.
2010/0081946 A1  4/2010  Garudadri et al.
(Continued)

FOREIGN PATENT DOCUMENTS

WO   WO-2013/036718            3/2013
WO   WO-2017212120 A1 * 12/2017 ........... A61B 5/0261

OTHER PUBLICATIONS

Ghosh et al, "Continuous blood pressure prediction from pulse transit time using ECG and PPG signals" 2016 IEEE Healthcare Innovation Point-Of-Care Technologies Conference (HI-POCT), Cancun, 2016, pp. 188-191, doi: 10.1109/HIC.2016.7797728. (Year: 2016).*

(Continued)

*Primary Examiner* — David J. McCrosky
*Assistant Examiner* — Chanel J Jhin
(74) *Attorney, Agent, or Firm* — Finnegan, Henderson, Farabow, Garrett & Dunner, LLP

(57) ABSTRACT

A method and system for blood pressure (BP) estimation of a person is provided. The system is estimating pulse transit time (PTT) using the ECG signal and PPG signal of the person. A plurality of features are extracted from the PPG. The plurality of PPG features and the PTT are provided as inputs to an automated feature selection algorithm. This algorithm selects a set of features suitable for BP estimation. The selected features are fed to a classifier to classify the database into low/normal BP range and a high BP range. The correctly classified normal BP data are then used to create a (Continued)

regression model to predict BP from the selected features. The current methodology uses automated feature selection mechanism and also employs a block to reject extreme BP data. Thus the available accuracy in predicting BP is expected to be more than the existing BP estimation methods.

8 Claims, 4 Drawing Sheets

(51) Int. Cl.
  *A61B 5/00* (2006.01)
  *A61B 5/0245* (2006.01)
  *A61B 5/352* (2021.01)
(52) U.S. Cl.
  CPC ............ *A61B 5/352* (2021.01); *A61B 5/7264* (2013.01); *A61B 5/7278* (2013.01); *A61B 5/7282* (2013.01)

(58) Field of Classification Search
  USPC .......................................................... 600/485
  See application file for complete search history.

(56) References Cited

U.S. PATENT DOCUMENTS

| | | |
|---|---|---|
| 2014/0031646 A1 | 1/2014 | Yakirevich et al. |
| 2015/0045713 A1 | 2/2015 | Attallah et al. |
| 2018/0185643 A1* | 7/2018 | Lee .................... A61B 5/02116 |

OTHER PUBLICATIONS

Muntner et al, "Systolic blood pressure goals to reduce cardiovascular disease among older adults." The American journal of the medical sciences vol. 348,2 (2014): 129-34. doi:10.1097/MAJ. 0000000000000314 (Year: 2014).*

* cited by examiner

METHOD AND SYSTEM FOR CUFFLESS BLOOD PRESSURE ESTIMATION USING PHOTOPLETHYSMOGRAM FEATURES AND PULSE TRANSIT TIME

CROSS-REFERENCE TO RELATED APPLICATIONS AND PRIORITY

The present application claims priority from Indian non-provisional specification no. 201721006574 filed on 23 Feb. 2017, the complete disclosure of which, in its entirety is herein incorporated by references.

TECHNICAL FIELD

The present application generally relates to the field of non-invasive blood pressure estimation. More particularly, but not specifically, the invention provides a system and method for estimation of blood pressure of a person using photoplethysmogram and pulse transit time.

BACKGROUND

Measurement of various physiological parameters, such as blood pressure of a person is typically performed in a clinical setting. Blood pressure is one of the important signs about the person's physical attributes and usefully indicates cardiovascular diseases. Therefore, the measurement/estimation of blood pressure has gained increasing attention. One can measure blood pressure in one of the two ways, that is, invasive and non-invasive methods. Although the accuracy of invasive method is high, it carries great risks and thus is restricted to a hospital setting in critical care. The most popular non-invasive blood pressure measurement techniques are auscultatory and oscillometric. These two methods involve occlusion of blood flow using an inflatable cuff. The sphygmomanometer is an auscultatory technique. As the auscultatory method is non-invasive, easy, and safe, it is well supported and has been accepted as standard method for clinical measurement despite the inaccuracy due to both observer errors and methodological errors. However, rather than using a stethoscope, a calibrated electronic pressure transducer is used to monitor the pressure oscillations within the cuff. Since it is also non-invasive, easy, safe, and furthermore eliminates the mercury column, the oscillometric technique is used primarily in automated non-invasive blood pressure devices. Common limitations of measurement include the reliance on blood flow and selection of an inappropriate cuff size and position.

With the rapid increase of cardiovascular diseases non-invasive cuff-less measurement methods are more commonly required for routine examinations and monitoring. In this regard, a large number of studies have been conducted and it has been observed that the pulse transit time (PTT) is an important physiological parameter that it is closely related to arterial stiffness and can be used to estimate the blood pressure of the person. PTT can be determined as the time delay from the R wave peak of electrocardiogram (ECG) to a characteristic point of finger photoplethysmogram (PPG) in the same cardiac cycle.

However, one of the main problems in blood pressure estimation analysis is uncertainty. Some of the sources of this uncertainty include imprecision in computations and vagueness in class definition. Various methods in the prior arts have used PTT as a parameter for the estimation of blood pressure, but most fail to distinguish between extreme and normal BP values with high accuracy, therefore there is still scope for the improvement.

SUMMARY OF THE INVENTION

The following presents a simplified summary of some embodiments of the disclosure in order to provide a basic understanding of the embodiments. This summary is not an extensive overview of the embodiments. It is not intended to identify key/critical elements of the embodiments or to delineate the scope of the embodiments. Its sole purpose is to present some embodiments in a simplified form as a prelude to the more detailed description that is presented below.

In view of the foregoing, an embodiment herein provides a system for estimating blood pressure (BP) of a person. The system comprises an ECG sensor, a PPG sensor, a memory and a processor. The ECG sensor captures an electrocardiogram (ECG) signal of the person. The PPG sensor captures a photoplethysmogram (PPG) signal of the person. The PPG signal is synchronized with the ECG signal. The processor is in communication with the memory. The processor further comprises a preprocessor, pulse transit time estimation module, a feature extraction module, an input module, a feature selection module, a classification module and a regression analysis module. The preprocessor preprocesses the ECG signal and PPG signal to remove a plurality of noises. The pulse transit time estimation module estimates a pulse transit time (PTT) using the ECG signal and PPG signal. The feature extraction module extracts a plurality of features of the PPG signal. The input module provides the PTT and the plurality of features to a feature selection module. The feature selection module applies a feature selection algorithm for selecting a set of features. The set of features are selected to maximize the accuracy in classifying a low/normal BP class from a high BP class. The classification module classifies the data corresponding to ECG signal, PPG signal and PTT in to the high BP class and the low/normal BP class based on the selected set of features. The regression analysis module performs the regression analysis on the PPG features and the PTT corresponding to the low/normal BP class to estimate the blood pressure of the person.

Another embodiment provides a method for estimating a blood pressure (BP) of a person. Initially, an electrocardiogram (ECG) signal of the person is captured using an ECG sensor. And a photoplethysmogram (PPG) signal of the person is captured using a PPG sensor. The PPG signal is synchronized with the ECG signal. In the next step, the ECG signal and PPG signal are preprocessed to remove a plurality of noises. Further, a pulse transit time (PTT) is estimated using the ECG signal and PPG signal, followed by the estimation of a plurality of features of the PPG signal. The PTT and the plurality of features are then sent to a feature selection module. In the next step, a feature selection algorithm is applied for selecting a set of features. The set of features are selected in a way as to maximize the accuracy in classifying a low/normal BP class from a high BP class. Then, the data corresponding to ECG signal, PPG signal and PTT is classified in to the high BP class and the low/normal BP class based on the selected set of features using a classification module. And finally the regression analysis is performed on the ECG signal, the PPG signal and the PTT corresponding to the low/normal BP class to estimate the blood pressure of the person.

In another embodiment, a non-transitory computer-readable medium having embodied thereon a computer program for estimating a blood pressure (BP) of a person. Initially, an electrocardiogram (ECG) signal of the person is captured using an ECG sensor. And a photoplethysmogram (PPG) signal of the person is captured using a PPG sensor. The PPG signal is synchronized with the ECG signal. In the next step, the ECG signal and PPG signal are preprocessed to remove a plurality of noises. Further, a pulse transit time (PTT) is estimated using the ECG signal and PPG signal, followed by the estimation of a plurality of features of the PPG signal. The PTT and the plurality of features are then sent to a feature selection module. In the next step, a feature selection algorithm is applied for selecting a set of features. The set of features are selected in a way as to maximize the accuracy in classifying a low/normal BP class from a high BP class. Then, the data corresponding to ECG signal, PPG signal and PTT is classified in to the high BP class and the low/normal BP class based on the selected set of features using a classification module. And finally the regression analysis is performed on the ECG signal, the PPG signal and the PTT corresponding to the low/normal BP class to estimate the blood pressure of the person.

BRIEF DESCRIPTION OF THE DRAWINGS

The embodiments herein will be better understood from the following detailed description with reference to the drawings, in which.

The Figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION OF EMBODIMENTS

The embodiments herein and the various features and advantageous details thereof are explained more fully with reference to the non-limiting embodiments that are illustrated in the accompanying drawings and detailed in the following description. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Figure 1:
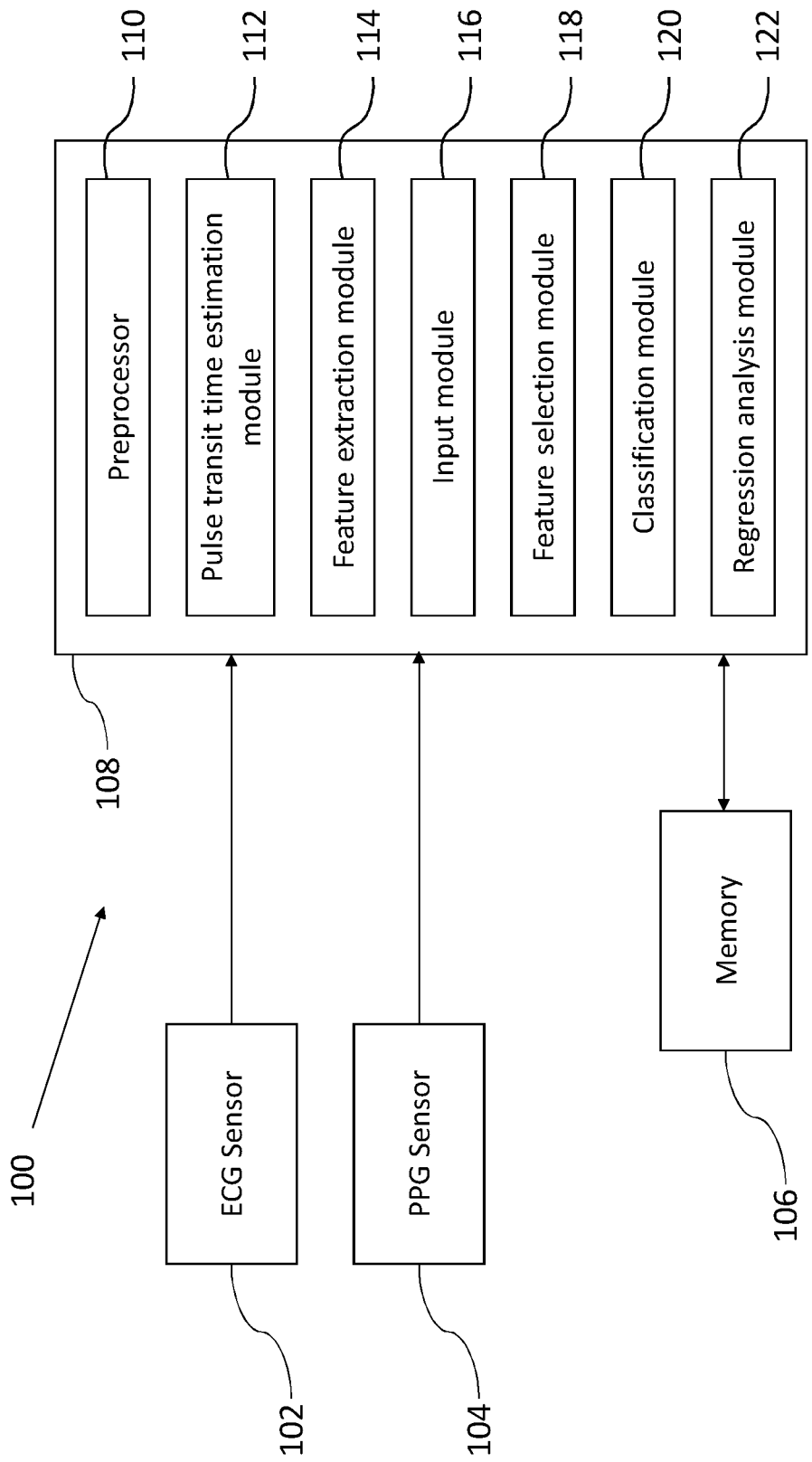
FIG. 1 illustrates a block diagram of a system for estimating a blood pressure (BP) of a person using pulse transit time, in accordance with an embodiment of the present disclosure.

Referring now to the drawings, and more particularly to FIG. 1, where similar reference characters denote corresponding features consistently throughout the figures, there are shown preferred embodiments and these embodiments are described in the context of the following exemplary system and/or method.

According to an embodiment of the disclosure, a system 100 for estimating a blood pressure (BP) of a person is shown in FIG. 1. The system 100 provides a non-invasive cuff-less technique for the estimation of the blood pressure of the person. The disclosure uses pulse transit time (PTT) as one of most important parameter for the estimation of the blood pressure. The system 100 classifies the normal/low BP class with high BP class and estimates the blood pressure with higher accuracy.

According to an embodiment of the disclosure, the system 100 comprises an ECG sensor 102, a PPG sensor 104, a memory 106 and a processor 108 in communication with the memory 106. The processor 108 is configured to read a plurality of algorithms stored in the memory to perform various functions. The processor 108 further includes a plurality of modules such as a preprocessor 110, a pulse transit time estimation module 112, a feature extraction module 114, an input module 116, a feature selection module 118, a classification module 120 and a regression analysis module 122.

According to an embodiment of the invention, an ECG signal of the person is captured using the ECG sensor 102. It should be appreciated that the use of any kind of ECG sensor 102 is well within the scope of this disclosure. The ECG signal is a graphic recording or display of the time variant voltages produced by the myocardium during the cardiac cycle. The P, Q, R, S and T reflect the rhythmic electrical depolarization and re-polarization of the myocardium associated with the contraction of the atria and ventricles.

According to an embodiment a PPG signal is captured using the PPG sensor 104. The PPG signal is based on the determination of the optical properties of a selected skin area. For this purpose nonvisible infrared light is emitted into the skin. More or less light is absorbed, depending on the blood volume. Blood volume changes can then be determined by measuring the reflected/transmitted light. It should be appreciated that the captured PPG signal is synchronized with the captured ECG signal. Generally the captured ECG signal and the PPG signals contain a plurality of noises. Therefore the ECG signal and the PPG signal are preprocessed using the preprocessor 110. The preprocessor 110 uses various pre-processing techniques like baseline and topline corrections and histogram based cycle selection strategies etc.

Figure 2:
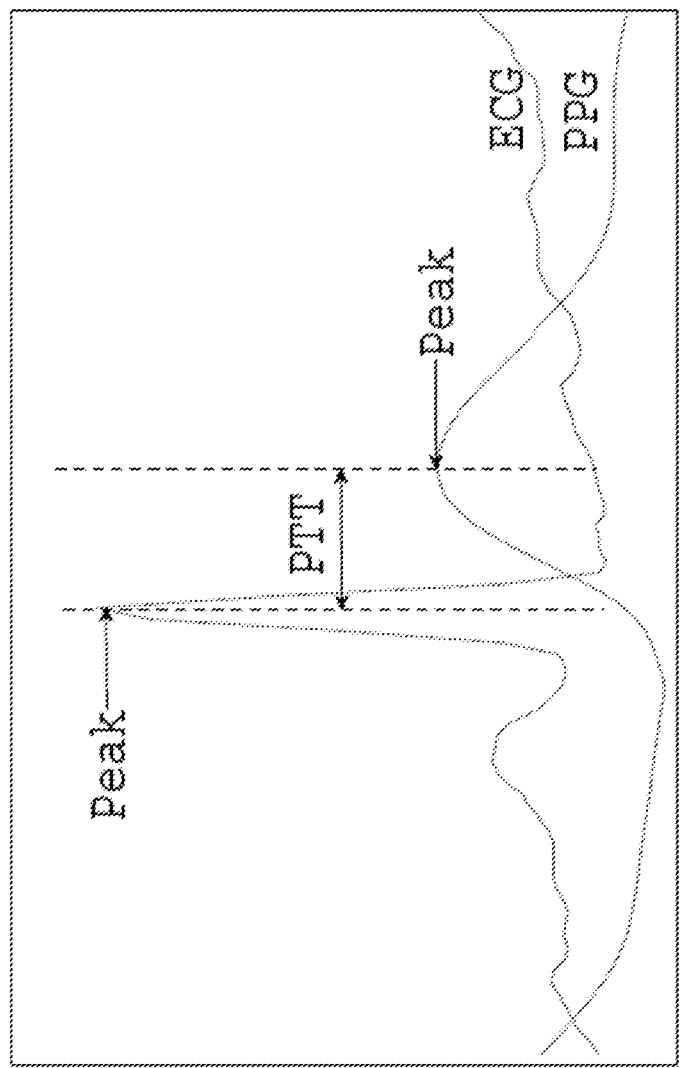
FIG. 2 is a graphical representation of PPG signal, ECG signal and pulse transit time, in accordance with an embodiment of the present disclosure.

According to an embodiment of the disclosure, the processor 108 further calculates the pulse transit time (PTT) for the person using the pulse transit time estimation module 112. PTT is the time taken by a pulse wave to propagate from heart of the person to a specified point on the body where the reading is taken, normally the finger or ear lobe. PTT is defined as the time duration from a reference point of time, for the pulse pressure wave to travel to any specified point on the periphery. Blood pressure changes, heart rate and the compliance of the arterial walls, and so on influence the PTT. The stiffness and tension in the arterial walls are the principle factors determining the speed of transmission of the pulse wave, and this in turn depends to a large extent on blood pressure. An increase in BP increases arterial wall tension and stiffness, thus shortening PTT; and conversely, a drop in BP lessens the stiffness and tension in the arterial walls, thus lengthening PTT. In an embodiment of the disclosure PTT is calculated as the time delay from the R wave peak of ECG signal to a peak point of finger photoplethysmogram in the same cardiac cycle as shown in the waveform of FIG. 2. It indicates that given a cardiac cycle the difference between the peak of PPG and R peak of ECG is used to calculate PTT.

According to an embodiment of the disclosure, the processor 108 also comprises the feature extraction module 114.

The feature extraction module 114 extracts a plurality of features of the PPG signal. The plurality of features may include time domain features, frequency domain features and HRV features. The example of time domain features include systolic and diastolic time durations, systolic and diastolic areas, cycle duration, systolic and diastolic time and area ratios, ratio of pulse widths at different pulse heights etc. Once the features are extracted, then a feature matrix can be created containing PTT and the plurality of PPG features.

Generally, the extracted plurality of features are large in quantity therefore only a set of features are selected out of the plurality of features using the feature selection module 118. The PTT and the plurality of features of the PPG signal are provided to the feature selection module 118 using the input module 116. The feature selection module 118 applies a feature selection algorithm for selecting the set of features. The set of features are selected in such a way that to maximize the accuracy in classifying a low/normal BP class from a high BP class. It should be appreciated that the present disclosure is measuring the systolic BP of the person. It should also be appreciated that, the systolic BP value of more than 150 mm Hg is considered as high BP, while anything below this value will be considered as the low/normal BP.

According to an embodiment of the disclosure, different feature selection algorithms may be used for selecting the set of features. In an example, these algorithms may be minimum redundancy maximum relevance (mRMR) algorithm, maximum relevance maximum significance (mRMS) algorithm and µHeM algorithm. The mRMR algorithm is a mutual information based method that selects a set of features by minimizing redundancy and maximizing relevance. While calculating redundancy between two features it does not consider class label information. On the other hand mRMS algorithm is a rough set based feature selection algorithm that selects a set of features by maximizing both relevance as well as significance and it incorporates class label information while calculating significance of a feature with respect to other features. For selecting features using the mRMR and mRMS algorithms the data set has to be in discretized form. In the process of discretization information loss in inevitable. However, the µHEM algorithm can handle real valued data. It is a rough hypercuboid based method that selects a set of features by maximizing both relevance and significance. The relevance and significance are calculated based on rough hypercuboid concept. It should be appreciated that the use of any other algorithm is well within the scope of this disclosure.

According to an embodiment of the disclosure, the processor 108 also includes the classification module 120. The classification module 120 classifies the low/normal BP class from the high BP class using a support vector machine (SVM) based method. It should be appreciated that the use of any other classification technique is well within the scope of this disclosure.

According to an embodiment of the disclosure, the data corresponding to ECG signal, PPG signal and PTT classified as low/normal BP are then provided to the regression analysis module 122. The regression analysis module 122 performs the regression analysis to estimate the blood pressure of the person. This way it improved the overall accuracy of the system 100. It is assumed that the regression analysis module 122 will provide a better accuracy when the high BP data are classified out previously.

Figure 3A:
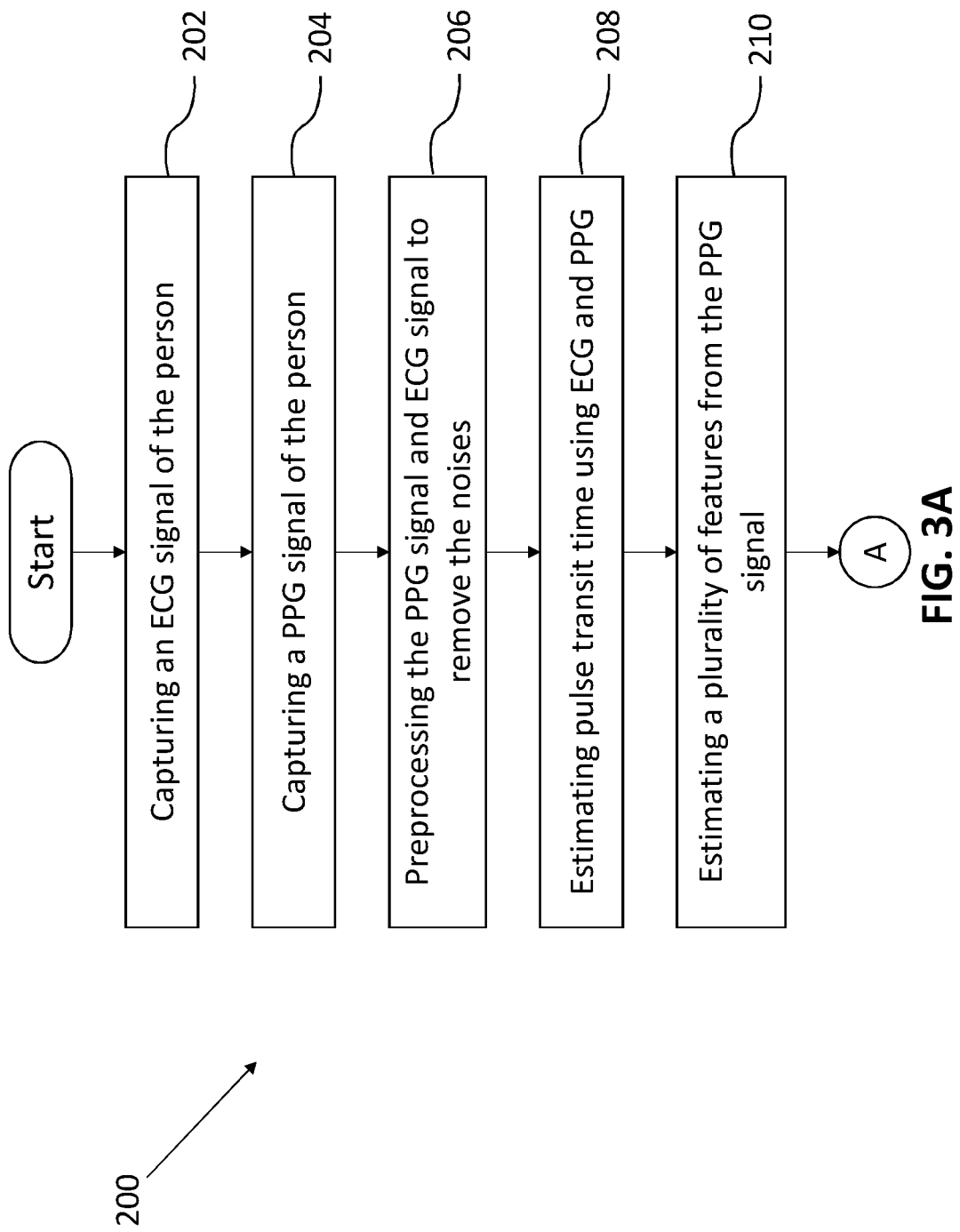
FIGS. 3A-3B is a flowchart illustrating the steps involved in the estimation of blood pressure (BP) of a person using pulse transit time, in accordance with an embodiment of the present disclosure.
Figure 3B:
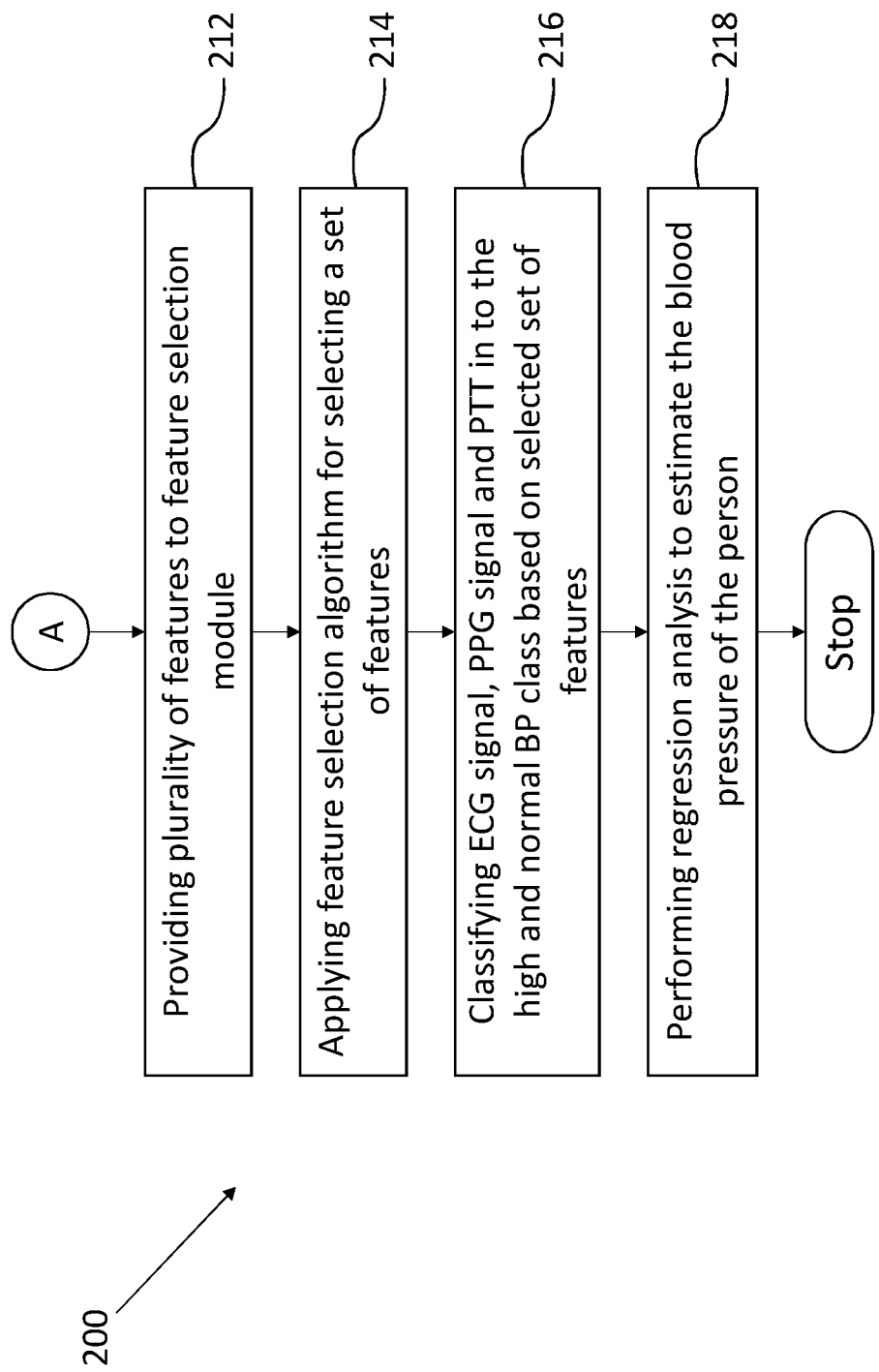

In operation, a flowchart 200 for estimating a blood pressure (BP) of a person is shown in FIGS. 3A-3B according to an embodiment of the disclosure. Initially at step 202, an electrocardiogram (ECG) signal of the person is captured using the ECG sensor 102. The use of any kind of ECG sensor 102 is well within the scope of this disclosure. At step 204, a photoplethysmogram (PPG) signal of the person is captured using the PPG sensor 104. It should be appreciated the capturing should be done in such a way that the PPG signal is synchronized with the ECG signal. At step 206, the ECG signal and PPG signal are preprocessed to remove a plurality of noises.

At step 208, the pulse transit time (PTT) is estimated using the ECG signal and PPG signal of the person. PTT is defined as the time duration from a reference point of time, for the pulse pressure wave to travel to any specified point on the periphery. In the next step 210, a plurality of features are extracted from the PPG signal. The plurality of features include time domain features, frequency domain features and the Heart Rate Variability (HRV) features. At step 212, the PTT and the plurality of features are provided to the feature selection module. In the next step 214, the feature selection algorithm is applied for selecting a set of features. The set of features are selected in such a way to maximize the accuracy in classifying a low/normal BP class from a high BP class. In the next step 216, the ECG signal, PPG signal and PTT are classified in to the high BP class and the low/normal BP class based on the selected set of features using a classification module. And finally, at step 218 the regression analysis is performed on the ECG signal, the PPG signal and the PTT corresponding to the low/normal BP class to estimate the blood pressure of the person.

In another embodiment, the accuracy of the estimated blood pressure value can be evaluated the using Bland Altman plot.

According to an embodiment of the disclosure, an experiment was also conducted to determine the relation between the blood pressure and the PTT. It has been found that the BP is inversely proportional to the PTT. The correlation between BP and PTT can be calculated using pearson correlation coefficient. It is the ratio between the covariance of two vectors (xi, xj) of feature values of two subjects and product of their standard deviations and is given by following equation:

$$\rho(x_i, x_j) = \frac{\text{Cov}(x_i, x_y)}{\sigma_{x_i}, \sigma_{x_j}};$$

that is, $$\rho(x_i, x_j) = \frac{\sum_{k=1}^{m}(x_{ik} - \bar{x}_i)(x_{jk} - \bar{x}_j)}{\sqrt{\sum_{k=1}^{m}(x_{ik} - \bar{x}_i)^2}\sqrt{\sum_{k=1}^{m}(x_{jk} - \bar{x}_j)^2}},$$

where $\bar{x}_i$ and $\bar{x}_j$ are the means of $x_{ik}$ and $x_{jk}$, respectively. It considers each feature as a random variable with m observations and measures the similarity between the two features by calculating the linear relationship between the distributions of the two corresponding random variables. The correlation between BP and PTT is calculated for multiple sessions of all the records using (2).

According to another embodiment of the disclosure, the performance of different feature selection algorithms is also analyzed in terms of classification accuracy, sensitivity, and specificity of SVM classifier. The records are grouped into the low/normal BP class and high BP class. From the Table 1 below it is seen that the mRMR algorithm obtains highest LOOCV accuracy of 87.90% with 4 features. On the other hand rough set based maximum relevance maximum-significance (mRMS) algorithm attains 87.90% accuracy with 5 features. The rough hypercuboid based μHEM algorithm achieved highest accuracy of 88.71% with 18 features. Irrespective of any feature selection algorithm, the PTT feature is selected as the most potential feature. Results indicate that rough set based feature selection approaches can handle uncertainty, ambiguity, and incompleteness in class definition. The results indicate that in spite of domain knowledge of physiological sensing data the proposed approach can select relevant set of features that can generate better result in terms of accuracy, sensitivity, and specificity.

TABLE 1

PERFORMANCE OF DIFFERENT FEATURE SELECTION ALGORITHMS

| Index | mRMR | RSMRMS | μHEM |
|---|---|---|---|
| Accuracy (%) | 87.90 | 87.90 | 88.71 |
| Sensitivity | 0.871 | 0.871 | 0.887 |
| Specificity | 0.887 | 0.887 | 0.887 |
| No. of Features | 4 | 5 | 18 |

Further, all the feature selection algorithms select PTT as the most potential feature. Importance of PTT feature is shown in Table 2 below. In order to study the importance of PTT feature next a study is conducted, classification accuracy is calculated with PTT feature as well as other features that are selected by feature selection algorithms and without PTT feature. The classification accuracy of the SVM classifier is shown with PTT feature and without PTT feature. From the table it is seen that the with PTT feature the classification accuracy improves. Hence, it signifies that the PTT is very important physiological parameter for estimation of BP.

TABLE 2

IMPORTANCE OF PTT

| Algorithms | | With PTT | Without PTT |
|---|---|---|---|
| mRMR | Accuracy (%) | 87.90 | 86.29 |
| | No. of Features | 4 | 3 |
| RSMRMS | Accuracy (%) | 87.90 | 87.90 |
| | No. of Features | 5 | 7 |
| μHEM | Accuracy (%) | 88.71 | 87.90 |
| | No. of Features | 18 | 11 |

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims. The embodiment, thus provides the system and method for testing of active molecules using simulation of skin membrane It is, however to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

A representative hardware environment for practicing the embodiments may include a hardware configuration of an information handling/computer system in accordance with the embodiments herein. The system herein comprises at least one processor or central processing unit (CPU). The CPUs are interconnected via system bus to various devices such as a random access memory (RAM), read-only memory (ROM), and an input/output (I/O) adapter. The I/O adapter can connect to peripheral devices, such as disk units and tape drives, or other program storage devices that are readable by the system. The system can read the inventive instructions on the program storage devices and follow these instructions to execute the methodology of the embodiments herein.

The system further includes a user interface adapter that connects a keyboard, mouse, speaker, microphone, and/or other user interface devices such as a touch screen device (not shown) to the bus to gather user input. Additionally, a communication adapter connects the bus to a data processing network, and a display adapter connects the bus to a display device which may be embodied as an output device such as a monitor, printer, or transmitter, for example.

The preceding description has been presented with reference to various embodiments. Persons having ordinary skill in the art and technology to which this application pertains will appreciate that alterations and changes in the described structures and methods of operation can be practiced without meaningfully departing from the principle, spirit and scope.

What is claimed is:

1. A method for estimating a blood pressure (BP) of a person, the method comprising a processor implemented steps of:
   capturing an electrocardiogram (ECG) signal of the person using an ECG sensor (102);
   capturing a photoplethysmogram (PPG) signal of the person using a PPG sensor (104), wherein the PPG signal is synchronized with the ECG signal;
   preprocessing the ECG signal and the PPG signal to remove a plurality of noises;
   estimating a pulse transit time (PTT) using the ECG signal and the PPG signal;
   extracting a plurality of features of the PPG signal, wherein the plurality of features of the PPG signal include time domain features, frequency domain features and heart rate variability (HRV) features, and wherein the time domain features of the PPG signal include systolic and diastolic time durations, systolic and diastolic time ratios, systolic and diastolic areas, systolic and diastolic area ratios, cycle duration, and ratio of pulse widths at different pulse heights;
   providing the PTT and the plurality of features to a feature selection module (118);
   applying a feature selection algorithm for selecting a set of features from the extracted plurality of features of the PPG signal, wherein the set of features are selected to maximize accuracy in classifying a low/normal BP class from a high BP class;
   classifying data corresponding to the ECG signal, the PPG signal and the PTT into the high BP class and the low/normal BP class based on the selected set of features using a classification module (120); and
   performing a regression analysis on the ECG signal, the PPG signal and the PTT corresponding to the low/normal BP class to estimate the BP of the person.

2. The method of claim 1 further includes the step of creating a feature matrix containing PTT and the plurality of PPG features.

3. The method of claim 1, wherein the feature selection algorithm is at least one of a maximum relevance minimum redundancy (mRMR) algorithm, a maximum relevance maximum significance (mRMS) algorithm or a µHEM algorithm.

4. The method of claim 1 wherein the classification module is a support vector machine (SVM) classifier designed using the selected set of features.

5. The method of claim 1, wherein the high BP class is with systolic BP more than or equal to 150 mmHg and normal/low BP class is with systolic BP less than 150 mmHg.

6. The method of claim 1 further include the step of evaluating the accuracy of the estimated BP using Bland Altman plot.

7. A system for estimating a blood pressure (BP) of a person, the system comprising:
   an electrocardiogram (ECG) sensor (102) for capturing an ECG signal of the person;
   a photoplethysmogram (PPG) sensor (104) for capturing a PPG signal of the person, wherein the PPG signal is synchronized with the ECG signal;
   a memory (106); and
   a processor (108) in communication with the memory, wherein the processor further comprises:
   a preprocessor (110) for preprocessing the ECG signal and the PPG signal to remove a plurality of noises,
   a pulse transit time estimation module (112) for estimating a pulse transit time (PTT) using the ECG signal and the PPG signal,
   a feature extraction module (114) for extracting a plurality of features of the PPG signal, wherein the plurality of features of the PPG signal include time domain features, frequency domain features and heart rate variability (HRV) features, and wherein the time domain features of the PPG signal include systolic and diastolic time durations, systolic and diastolic time ratios, systolic and diastolic areas, systolic and diastolic area ratios, cycle duration, and ratio of pulse widths at different pulse heights,
   an input module (116) for providing the PTT and the plurality of features to a feature selection module,
   a feature selection module (118) for applying a feature selection algorithm for selecting a set of features from the extracted plurality of features of the PPG signal, wherein the set of features are selected to maximize the accuracy in classifying a low/normal BP class from a high BP class,
   a classification module (120) for classifying the ECG signal, the PPG signal and the PTT into the high BP class and the low/normal BP class based on the selected set of features, and
   a regression analysis module (122) for performing a regression analysis on the ECG signal, the PPG signal and the PTT corresponding to the low/normal BP class to estimate the BP of the person.

8. A non-transitory computer-readable medium having embodied thereon a computer program for estimating a blood pressure (BP) of a person, the method comprising a processor implemented steps of:
   capturing an electrocardiogram (ECG) signal of the person using an ECG sensor (102);
   capturing a photoplethysmogram (PPG) signal of the person using a PPG sensor (104), wherein the PPG signal is synchronized with the ECG signal;
   preprocessing the ECG signal and the PPG signal to remove a plurality of noises;
   estimating a pulse transit time (PTT) using the ECG signal and the PPG signal;
   extracting a plurality of features of the PPG signal, wherein the plurality of features of the PPG signal include time domain features, frequency domain features and heart rate variability (HRV) features, and wherein the time domain features of the PPG signal include systolic and diastolic time durations, systolic and diastolic time ratios, systolic and diastolic areas, systolic and diastolic area ratios, cycle duration, and ratio of pulse widths at different pulse heights;

providing the PTT and the plurality of features to a feature selection module (118);

applying a feature selection algorithm for selecting a set of features from the extracted plurality of features of the PPG signal, wherein the set of features are selected to maximize the accuracy in classifying a low/normal BP class from a high BP class;

classifying data corresponding to the ECG signal, the PPG signal and the PTT into the high BP class and the low/normal BP class based on the selected set of features using a classification module (120); and performing a regression analysis on the ECG signal, the PPG signal and the PTT corresponding to the low/normal BP class to estimate the BP of the person.

* * * * *